United States Patent
Stolle et al.

(10) Patent No.: US 6,538,728 B1
(45) Date of Patent: Mar. 25, 2003

(54) GAS SENSOR WITH OPEN OPTICAL MEASUREMENT PATH

(75) Inventors: Ralf Stolle, Lubeck (DE); Hartmut Stark, Stockelsdorf (DE)

(73) Assignee: Dräger Sicherheitstechnik GmbH, Lubek (DE)

( * ) Notice: Subject to any disclaimer, the term of this patent is extended or adjusted under 35 U.S.C. 154(b) by 98 days.

(21) Appl. No.: 09/593,517

(22) Filed: Jun. 15, 2000

(30) Foreign Application Priority Data

Aug. 26, 1999 (DE) .......................................... 199 40 280

(51) Int. Cl.⁷ .............................................. G01N 21/61
(52) U.S. Cl. ........................................................ 356/237
(58) Field of Search .................................. 356/437, 438

(56) References Cited

U.S. PATENT DOCUMENTS

| | | | |
|---|---|---|---|
| 4,160,246 A | * 7/1979 | Martin et al. | 356/438 |
| 4,225,245 A | * 9/1980 | Roiret et al. | 356/447 |
| 5,339,155 A | 8/1994 | Partridge | |
| 5,371,367 A | 12/1994 | DiDomenico et al. | 250/338 |
| 5,404,228 A | * 4/1995 | McGowan | 356/438 |
| 5,459,574 A | * 10/1995 | Lee et al. | 356/437 |
| 5,591,975 A | 1/1997 | Jack et al. | |
| 5,767,976 A | 6/1998 | Ankerhold et al. | |
| 5,831,730 A | * 11/1998 | Traina et al. | 356/439 |
| 6,044,329 A | * 3/2000 | Kidd | 356/301 |

FOREIGN PATENT DOCUMENTS

| | | |
|---|---|---|
| DE | 39 02 015 | 7/1991 |
| DE | 195 35 679 | 3/1996 |
| DE | 196 11 290 | 4/1998 |
| DE | 199 40 280 C2 | 3/2001 |
| GB | 2057121 A | 3/1981 |
| GB | 2274163 A | 7/1994 |
| GB | 2353591 | 2/2001 |

* cited by examiner

Primary Examiner—Richard A. Rosenberger
(74) Attorney, Agent, or Firm—Nixon & Vanderhye P.C.

(57) ABSTRACT

The invention relates to a gas sensor with an open optical measurement path for optical measurement of at least one gas component, having a light source unit (1), a detector unit (2), between which units the optical measuring path (13) extends, and having a control and evaluation device; the light source unit (1) has a light source (3) and optical guide elements for transmitting a measuring light beam to the detector unit (2), and the detector unit (2) includes a detector (4), which when oriented in the beam path of the measuring light beam detects the intensity of light from the measuring light beam, and the control and evaluation device (11) is designed to determine, on the basis of the measurement signal of the detector (4), a standard for the concentration of the gas component to be investigated. To simplify calibration and to simplify and broaden the operating functions, it is provided that the light source unit (1) is provided with a receiver device (9), which communicates with a control and evaluation device (6) in the light source unit (1), and the detector unit (2) is provided with a transmitter device (10), which communicates with the control and evaluation device (11) in the detector unit (2), so that a direct data exchange between the detector unit (2) and the light source unit (1) is made possible. In this way, it is for instance possible for the control and evaluation units, with the aid of controllable optical guide elements, to achieve an automatic optimization of the beam to the detector.

12 Claims, 5 Drawing Sheets

GAS SENSOR WITH OPEN OPTICAL MEASUREMENT PATH

CROSS-REFERENCES TO RELATED APPLICATIONS

This application is related to German patent application No. 19940280.9 filed on Aug. 26, 2000 whose priority is claimed under 35 USC §119, the disclosure of which is incorporated herein by reference in its entirety.

BACKGROUND OF THE INVENTION

1. Field of the Invention

The invention relates to a gas sensor with an open optical measurement path.

2. Description of the Related Art

One such device is known for instance from U.S. Pat. No. 5,591,975, in which a device for measuring the exhaust gases of automobiles driving past it is described. The vehicles traverse the measurement path, which is bounded on one by a light source and on the other by a field of photodiodes.

In environmental analysis and industrial monitoring, the analysis of gaseous mixtures has gained increasing significance. There is accordingly increasing interest in the development of novel gas sensors that are optimized with respect to their sensitivity, selectivity, service life, and ease of manipulation.

Along with gas sensors that monitor a spatially narrowly limited region, recently gas sensors that monitor a larger area are increasingly being employed. The so-called gas sensors with an open optical measurement path (or open path sensors) record the mean concentration of the target gas over a path with a length of ten meters to a few hundred meters.

U.S. Pat. No. 5,339,155 describes a device in which the light of a light source is modulated in its wavelength, and this frequency modulation is converted, in the presence of the target gas, into an amplitude modulation that can be measured by a detector. The path is bounded, that is, defined, by a light source unit and a detector unit that are spatially separate from one another.

As light sources, laser light sources have increasingly been used in recent years. DFB laser diodes, in particular, are distinguished in that on the one hand the wavelength of the emitted light is very much narrower in its band than the absorption lines of gases, and on the other, this wavelength can be varied both by way of the temperature of the laser diode and via the triggering laser diode current.

In many laser diode-supported systems, so-called derivative spectroscopy is employed. In it, the wavelength of the laser diode is initially set, for instance by specifying the laser diode temperature, in such a way that the very narrow-band laser line is located spectrally within the absorption of a single gas line, for instance, of the target gas. The desired monitoring of the laser diode temperature can be performed for example by locating the laser diode chip on a Peltier element, which can be brought to a desired temperature by varying the Peltier current. The laser diode is operated with a current modulation in such a way that the gas line is periodically swept at the frequency f, and the modulation is preferably sinusoidal. Not only is the laser diode varied in its wavelength, but furthermore, as a parasitic effect, an amplitude modulation of the radiation intensity at the frequency f, the so-called $1f$ component, also occurs, and this amplitude modulation can be utilized to standardize the intensity.

Once the measurement path has been traversed, the intensity of the light is detected with a detector sensitive to the light of the light source; the detector generates an electrical signal that is proportional to the incident light intensity. This detector is equipped with an optical filter, which filters out interfering components of the spectrum, such as incident daylight. In the absence of the target gas, the detector signal is likewise sinusoidal at the frequency f, because of the corresponding amplitude modulation of the laser diode current. If target gas is present within the measurement path, however, then the intensity measured by the detector after the path has been traversed includes, as a function of time, components that are modulated with n-times the frequency, which are known as $n^{th}$ harmonic components or $n^{th}$ harmonics. The generation of these harmonic components is dictated by the nonlinear curvature of the absorption line of the gas. With the aid of suitable phase-sensitive measuring amplifiers (known as lock-in amplifiers], these harmonic components of the detector signal can be determined. While the $1f$ component of the detector signal is influenced hardly at all by the gas concentration, the higher $2f$, $3f$ and further components are approximately proportional to the gas concentration. Thus the quotient of the $2f$ component and the $1f$ component, for instance, known as the $2f:1f$ quotient, represents a standardized number for determining the gas concentration that is independent of such external effects as aging of the light sources, and broad-band attenuation from dirt, fog, and so forth.

To compensate for zero drift and to increase the sensitivities, the fast $1f$ modulation of the laser diode wavelength is additionally underlayed by a slower modulation of the mean wavelength at the frequency F (f>F), by varying the laser diode current accordingly. This slow modulation can for instance be in the form of a linear tuning ramp (sawtooth); one period of this slow modulation is called "scan". During one scan, a previously defined number of n $2f:1f$ quotients at n different wavelengths is picked up. The amplitudes of both the fast f- and the slow F-modulation of the wavelength are each selected such that they correspond approximately to the width of the gas line. Thus instead of the single value of a $2f:1f$ quotient described previously for a fixed wavelength, a plurality or a tuplet of n $2f:1f$ quotients at n different wavelengths is now obtained. This measurement value tuplet can serve, with suitable mathematical evaluation, for instance by a PCA (Principal Components Analysis) process or the like, both to determine the target gas concentration and to identify the target gas with certainty.

To prevent the originally set temperature of the laser diode or the Peltier element from varying during operation and thus varying the wavelength of the laser light, a beam splitter is mounted on the side of the light source unit or the detector unit; it deflects part of the light emerging from the laser diode through a cell (reference cell) in which a gas of suitable absorption capacity—for instance, the target gas itself—is confined. This portion of the light is detected, after passing through the reference cell, by a light-sensitive detector. With the aid of a phase-sensitive measuring amplifier, analogously to the measurement tuplet, a set of reference measurement values, a so-called reference tuplet, can be determined that is preferably again composed of $2f:1f$ quotients. By a comparison of this reference tuplet with values stored in memory, it is possible to detect any wavelength drift and to correct the temperature of the laser diode in such a way that this wavelength drift is precisely compensated for.

Open path gas sensors, when there is a large three-dimensional spacing between the light source unit and the detector unit, can be manipulated upon assembly and in operation only with difficulty and at great effort. For instance in derivative spectroscopy, problems of adaptation arise between the control of the light source and the evaluation of the detector signals. As much as possible, adaptations between the control of the light source and the evaluation for the detector signals must be done in a separate control and evaluation device, which is in communication with both the light source unit and the detector unit.

Such adaptation and control problems can be partially avoided by gas sensor systems in which the light source unit and detector unit are disposed directly adjacent one another and a long open measurement path is realized by providing that the light source aims a measurement beam at a remotely located retroreflector, by which the measurement beam is reflected and thrown back at the detector unit. One such gas sensor is known from German Patent DE 196 11 290 C2, for instance. In this known gas sensor device, the light source unit and the detector unit are not accommodated separately from one another but rather in one housing. This gas sensor has the advantage that the light source unit and the detector unit can function, adapted to one another, in a simple way. A disadvantage of such gas sensors is the use of a retroreflector, because then the signal-to-noise ratio is less favorable than in gas sensors in which the measuring light from the light source is aimed directly at the detector unit.

Another problem in gas sensors with open paths of great length resides in calibrating the gas sensor. Since the light source unit and the detector unit can be several hundred meters apart, both in assembly and when the system is put into operation careful optical alignment of the two units with one another must first be done. This raises the following problems. First, the optical guide elements, which in both the light source unit and the detector unit serve to project the measurement light at the detector, are mounted rigidly in the light source unit and detector unit. Thus the entire light source unit and the entire receiver device must be moved to enable optimal calibration of the system. If the spacing between the light source unit and the detector unit is 100 meters, for instance, then the light source unit must be capable of being moved with a precision of 1/20°, if the measurement light in the detector unit is to be positionable with an accuracy of 10 cm. This demand for precision, along with the typical weight of the light source unit, which is several kilograms, is a major engineering problem in practical terms. Secondly, during the calibration of the system, information as to how good the calculation is at the moment is not immediately available. Thus either a course adjustment must be made first, using an optical aid such as a telescopic sight and then monitoring the detector signal at the detector 100 meters away, in which case either the mechanic himself must go to the remote detector unit, or else a second person has to record and monitor the detector signal there. Thus puffing a gas sensor with an open path of great length into operation or monitoring its calibration is possible only at high expense in terms of both labor and time.

SUMMARY OF THE INVENTION

It is therefore the object of the present invention to create a more easily manipulated and operated gas sensor with an optical measurement path that is easily adjustable even if the path is long. Furthermore, the measurement light of the light source unit should be aimed directly at the detector unit, rather via a retroreflector, so that a good signal-to-noise ratio is attainable, and at the same time simple adaptation between the detector unit and the light source unit should be made possible.

According to the invention, the detector unit is provided with a transmitter device and the light source unit is provided with a receiver device that responds to the signals of the transmitter device, so that a direct data exchange between the detector unit and the light source unit is made possible; the transmitter and receiver devices each communicate with control and evaluation devices in the detector unit and the light source unit. In this way it is possible, for instance, upon calibration of the gas sensor to undertake an optimization of the orientation of the light source unit and the detector unit to one another; the light source unit receives feedback of the detector signal detected from the detector unit, so that a scanning surge makes it possible to optimize the intensity of the detector signal, thus enabling optimal aiming of the measuring light beam at the detector unit. Such a feedback can also be used to perform an automatic calibration of the light source unit and detector unit. To that end, electrically triggerable, movable optical guide elements (mirrors) can be present in both the light source unit and in the detector unit and are adjusted by control and evaluation devices in such a way that the highest possible detector signal results, and thus the best possible orientation or aiming of the detector in the beam path of the measuring light beam is attained.

In an advantageous embodiment, conversely, the light source unit is also equipped with a transmitter device and the detector unit is also equipped with a receiver device that responds to this transmitter device, so that a direct bidirectional data exchange between the light source unit and the detector unit is made possible. The capability of a bidirectional data exchange between the light source unit and the detector unit has many advantages. For instance, servicing functions, calibration of the gas sensor, or a self-test can be performed by means of suitably designed control and evaluation devices in the light source unit and the detector unit. Especially in conjunction with the above-described derivative spectroscopy in combination with a laser diode, it is highly advantageous from the standpoint of measurement technology if a bidirectional data exchange between the light source unit and the detector unit is achieved, for instance for the sake of demodulating the detector signal or for synchronizing the control and evaluation device in the detector unit with the tuning ramp that triggers the laser diode and that is monitored by the control and evaluation device in the light source unit.

The transmitter and receiver devices in the light source unit and the detector unit can function either in wireless fashion or via a cable connection, either an electrical or an optical cable connection. Alternatively, it is also possible for the transmitter device in the light source unit to be realized by,. means of a suitable design of the control and evaluation device, which triggers the light source in such a way that the measured light is modulated in frequency and/or amplitude, so that by means of the measuring light, data can also be transmitted that can be demodulated from the detector signal by a suitably designed control and evaluation device in the detector unit.

The light source may be an incandescent lamp, flash bulb, laser diode or any other light source. The measuring light is not limited to the range of visible light, for instance; in many cases it is advantageous to work outside the range of visible light, for instance in the infrared range, so that interfering effects from background light and sunlight can be precluded.

DETAILED DESCRIPTION OF THE INVENTION

Figure 1:
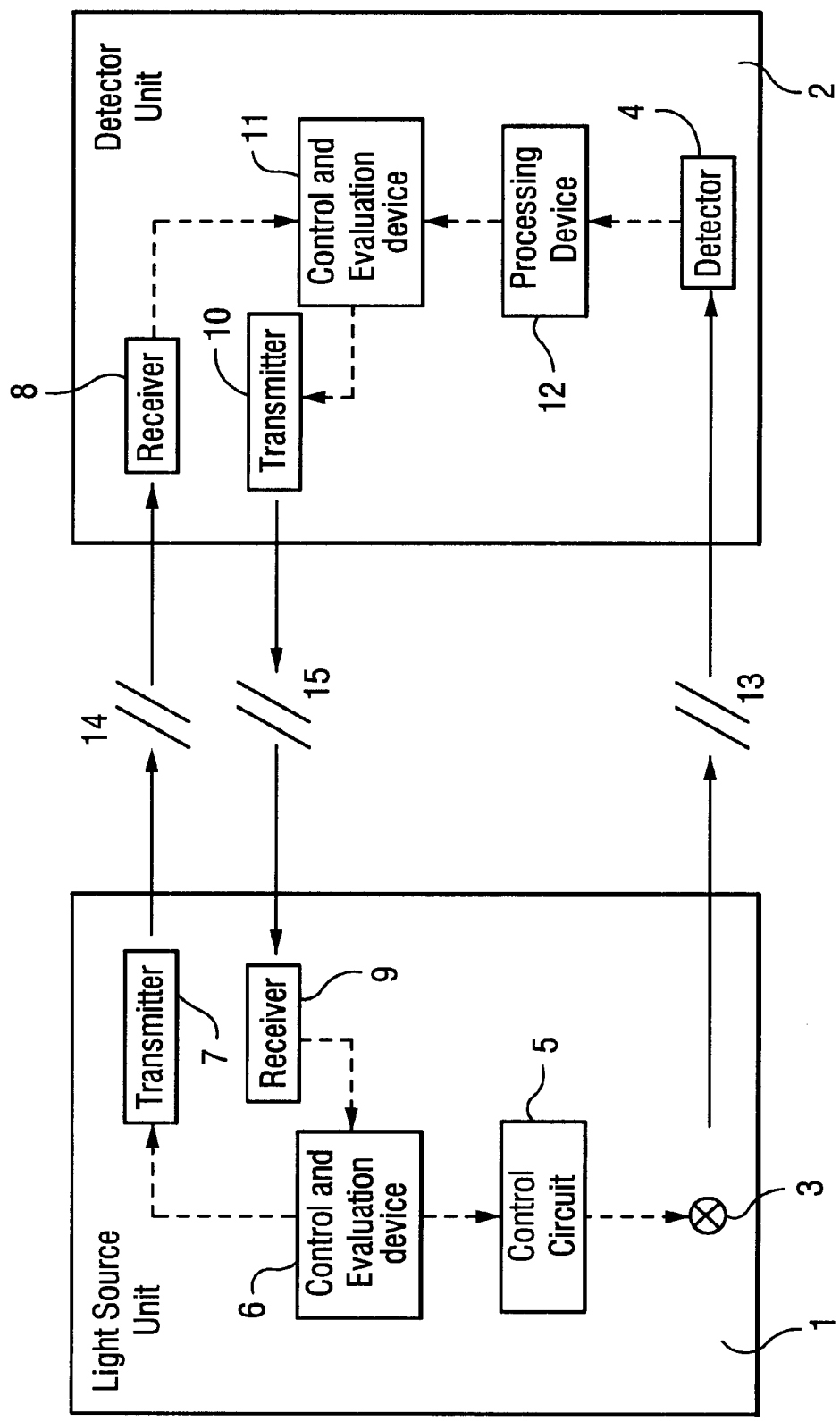
FIG. 1 is a schematic block diagram of a light source unit and a detector unit.

FIG. 1 shows an embodiment of the invention in which a bidirectional data transmission is provided between a light source unit 1 and a detector unit 2 via two communication channels 14, 15. The measuring light source 3 emits the measuring light and is triggered by a control circuit 5, which furnishes the light source 3 with the necessary supply parameters, such as current, voltage, and so forth, and which is controlled in turn by a control and evaluation device 6 in the form of a processor.

The measuring light traverses the open measuring path 13 and is recorded by a detector 4 in the detector unit 2. The measurement signal of the detector 4 is electrically preprocessed in the processing device 12; this preprocessing can comprise current to voltage conversion, preamplification, demodulation, analog to digital conversion, and so forth. Finally, the preprocessed signal is carried to a control and evaluation device 11 in the form of a processor, which performs the evaluation of the data and in particular from these data ascertains the gas concentration of the target gas in the path 13.

The communication channels 14 and 15 for bidirectional data exchange between the light source unit 1 and the detector unit 2 are formed by a transmitter device 7 in the form of a light source together with a trigger circuit and a first receiver device 8 in the form of a detector, as well as a transmitter device 10 in the form of a light source together with a trigger circuit and a second receiver device 9 in the form of a detector. The data exchange is controlled by the same control and evaluation devices 6 and 11 in the light source unit 1 and the detector unit 2 that also trigger or read out and evaluate the light source 3 and the detector 4, respectively.

Alternatively, instead of optical transmitter devices 7, 10 and receiver devices 8, 9, it is possible to use corresponding transmitter devices 7, 10 and receiver devices 8, 9 that use radio signals.

The embodiment shown in FIG. 1 can be used for instance in a laser diode supported gas sensor with an open measuring path that functions by the above-described method of derivative spectroscopy. Suitable data from the light source unit 1 can be sent to the detector unit 2, which enables synchronization of the control and evaluation device 6 with the triggering of the light source 3 by the control and evaluation device 6, for instance synchronization with the tuning ramp, which brings about the aforementioned slow displacement in the mean wavelength of the laser light. For example, at the very outset of each scan, a data flow (starting pulse) can be sent from the light source unit 1 to the detector unit 2 over the communication channel 14, which enables the control and evaluation device 11 in the detector unit 2 to synchronize itself with the tuning ramp of the triggering of the light source 3.

With the embodiment shown in FIG. 1, it is also possible to transmit data from the detector unit 2 to the light source unit 1 which provide information as to how strong the optical measuring light signal received by the detector 4 is. This information can be employed quite advantageously in a calibration of the system, for instance the first time it is put into operation, because the technician who aims the light source unit 1 or the light source 3 at the detector 4 can thereby obtain direct information about the quality of the calibration.

Figure 2:
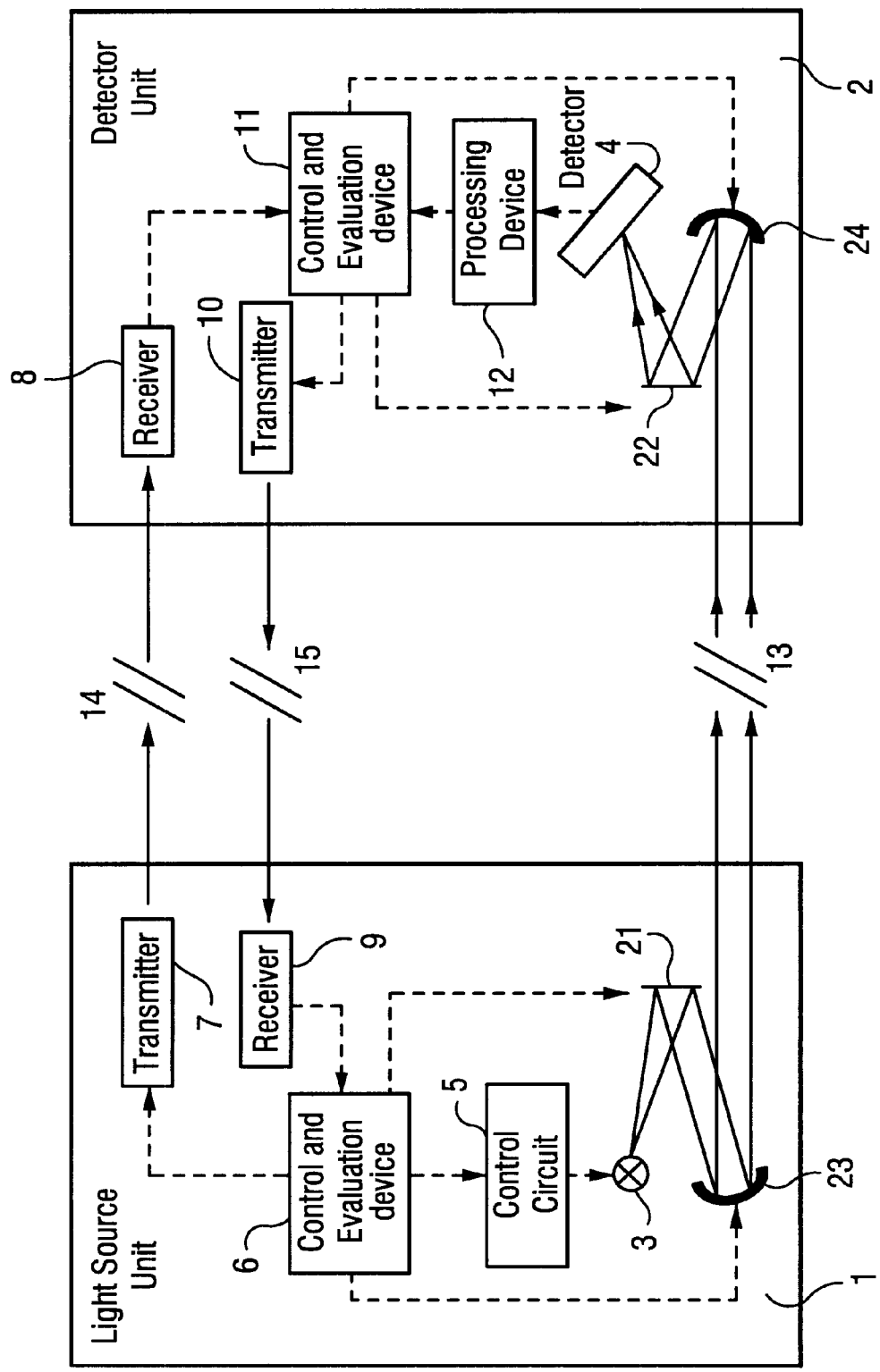
FIG. 2 shows a modification of the device shown in FIG. 1, in which optical guide elements that are electrically calibratable are provided in the light source unit and the detector unit.
Figure 3A:
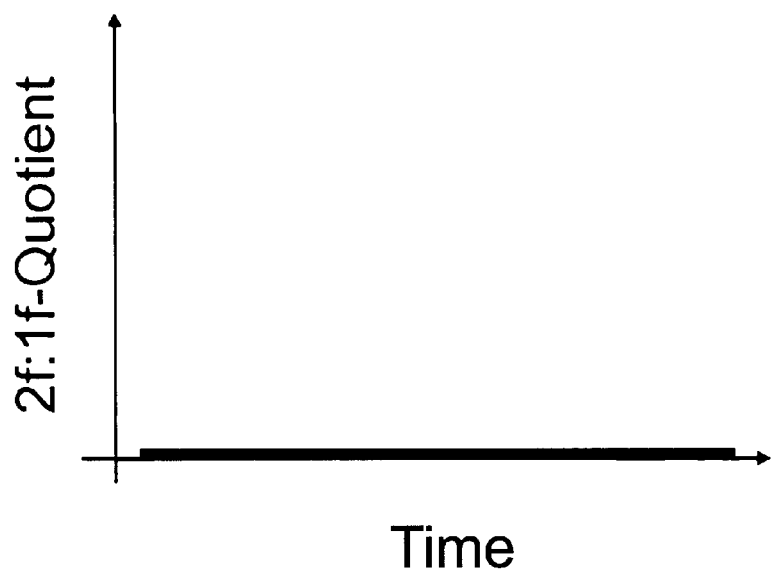
FIG. 3 shows the course of the 2f:1f quotient in a laser diode-supported gas sensor with an open measuring path during a scan, under the following conditions: (a) normal operating mode, when no target gas is present; (b) normal operating mode, when target gas is present; (c) monitoring scan, when no target gas is present; (d) monitoring scan, when target gas is present.
Figure 3B:
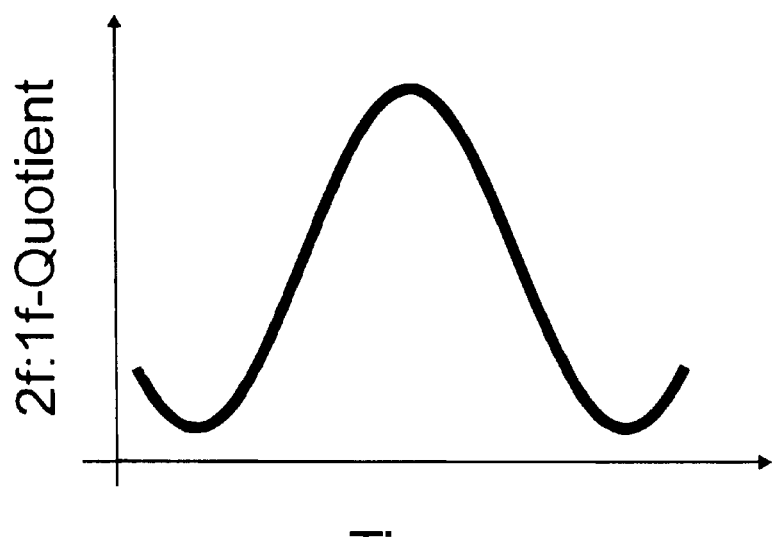
Figure 3C:
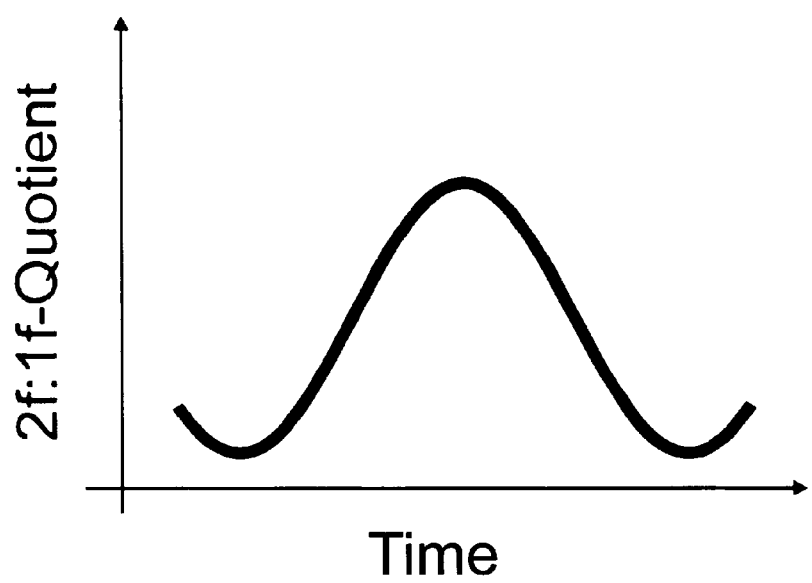
Figure 3D:
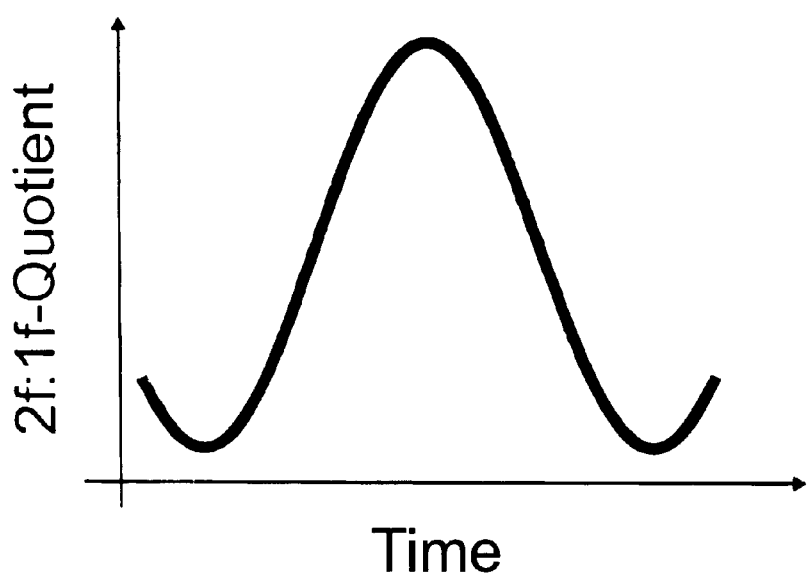

In a broadening of the embodiment shown in FIG. 1, it is possible for the gas sensor to adjust automatically, if the optical guide elements of the light source unit 1 and/or of the detector unit 2 are adjustable by electrical triggering, that is, if the corresponding optical guide elements are provided with an electrically triggerable calibration device. FIG. 2 shows one such exemplary embodiment, in which the optics of the light source unit 1 and detector unit 2 each comprise one curved mirror 23, 24 and one plane 21, 22, respectively, and in which these four mirrors are all adjustable independently of one another.

In the exemplary embodiment of FIG. 2, putting the gas sensor into operation is simplified substantially, since the optical calibration of the light source unit 1 and detector unit 2 can be done in such a way that initially only rough aiming is done, so that the detector 4 simply receives measuring light from the light source 3. The requisite fine adjustment for optimizing the optical aiming is then done automatically by the gas sensor by means of the calibration of the mirrors 21, 22, 23, 24, by designing the control and evaluation devices 6 and 11 accordingly so that they can execute optimizing search runs that lead to optimal adjustment of the mirrors and hence to an optimal measurement signal of the detector 4. A fine calibration of this kind can be done for instance in such a way that the mirrors 21, 23 of the light source unit 1 traverse a previously defined pattern of motion through which the light of the measuring light beam sweeps over the detector 4. By means of the transmitter device 10 and the receiver device 9, the detector unit 2 can inform the light source unit 1, or specifically its control and evaluation device 6, as to the instant at which the reception signal was optimal, or in other words at which position the highest intensity of the detector signal was for instance measured. The control and evaluation device 6 can reproduce this position so as then to initiate a second motion pattern, for instance, of the optical guide elements of the light source unit 1, in order feel its way iteratively to an optimally oriented position of the optical guide elements of the light source unit 1. Next, the optical guide elements of the detector unit 2, namely the mirrors 22 and 24, can likewise adjust themselves automatically and iteratively, to attain an optimal beam path and a maximum measuring light intensity at the detector 4.

Alternatively, it is possible to calibrate the optical guide elements of the light source unit 1 and/or detector unit 2 as a whole, with the relative orientation of the optical guide elements to one another, or in other words in FIG. 2 the orientation of mirror 21 to mirror 23 and of mirror 22 to mirror 24, remains unchanged.

With the embodiment shown in FIG. 2, it is also possible to perform the described automatic calibration of the system not only the first time it is put into operation but also, if the gas sensor becomes maladjusted, during operation as well so that a requisite recalibration can be performed automatically as needed.

In a further embodiment, it is possible to construct the gas sensor in such a way that with the measuring light itself, additional data are transmitted from the light source unit 1 to the detector unit 2, by suitable modulation of the light source 3. This capability can be achieved by providing that in FIG. 1, the control and evaluation device 6, for instance, is prepared so that it can modulate the light source 3 suitably via the light source trigger means 5. In the case of laser diode-supported derivative spectroscopy, the data are impressed on the triggering laser diode current, and in the laser diode, this current modulation is reconverted into an amplitude modulation of the measuring light, which can be recorded by the detector 4 and decoded and evaluated by the control and evaluation device 11.

It is thus possible for instance in derivative spectroscopy in conjunction with a laser diode to modulate the measuring light in such a way that the intensity of the laser light at the site of the detector 4 a priori, as a function of time, includes a $2f$ component, of the kind would usually be generated solely by the presence of the target gas within the path 13. FIGS. 3a–3d schematically show the $2f{:}1f$ quotient as it is measured during a scan: In the normal operating mode, the laser light is modulated purely sinusoidally with the frequency f, so that the signal received from the detector 4, in the absence of the target gas, has no, or only a very slight, $2f{:}1f$ component (see FIG. 3($a$)). In the presence of the target gas in the open measuring path 13, a characteristic course of the $2f{:}1f$ quotient arises during a scan, from which course a conclusion can be drawn about the gas concentration (see FIG. 3 ($b$)). With the capability offered according to the invention of exchanging data between the light source unit 1 and detector unit 2, it is possible at arbitrary times to transmit a so- called monitoring scan: Now—in contrast to the normal operating mode—the laser diode current itself already has a suitable $2f$ component imposed on it. This $2f$ component of the laser diode current is not constant during a scan but instead is varied in such a way that the $2f{:}1f$ quotient of the laser diode current has a form that except for a constant factor corresponds to the course of the $2f{:}1f$ quotient of FIG. 3($b$). Thus the emitted laser light from the very outset undergoes an amplitude modulation, which is so pronounced that the measured signal in the detector unit 2 can be misinterpreted by the control and evaluation device 11 as a gas concentration even if there was no target gas in the path 13.

FIGS. 3($c$) and 3($d$) illustrate the control scan. In the absence of the target gas, the measured $2f{:}1f$ quotient of the detector signal corresponds to the presence of the target gas at a certain concentration (pseudo gas concentration; see FIG. 3($c$)). This pseudo gas concentration can be selected freely beforehand by way of the scaling of the $2f$ component of the laser diode current. In the presence of the target gas (FIG. 3($d$)), the gas-dictated measuring effect is added to the $2f{:}1f$ quotient of the monitoring scan, so that overall, the gas detector measures a concentration that corresponds to the sum of the gas concentration and the pseudo gas concentration. By means of the capability, afforded with the gas sensor equipped according to the invention, of initiating such a monitoring scan at any arbitrary time, it is possible on the one hand to check the measuring readiness of the gas sensor at regular intervals. To that end, the condition can for instance be investigated as to whether the gas concentration measured during a monitoring scan is at least as high as the previously selected pseudo gas concentration; if not, some operating malfunction is occurring.

The described procedure with a monitoring scan can furthermore be utilized to monitor the calibration of the gas sensor. For the calibration, the fact can be exploited that the gas concentration measured after the initiation of a monitoring scan must be as high as the sum of the selected pseudo gas concentration and the gas concentration that was recorded in the normal operating mode immediately before the monitoring scan was initiated. If this is not the case, then a malfunction of the gas sensor or erroneous calibration is involved.

Figure 4A:
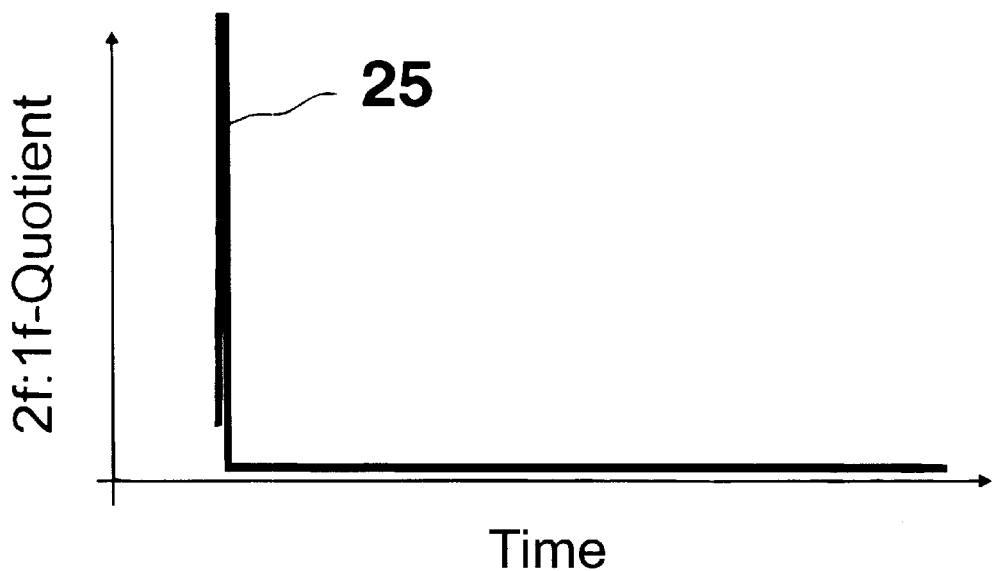
FIG. 4 shows the course of the 2f:1f quotient in a laser diode-supported gas sensor with an open measuring path during a scan with a starting pulse for synchronizing the light source unit and detector unit, in the presence (a) and absence (b) of the target gas.
Figure 4B:
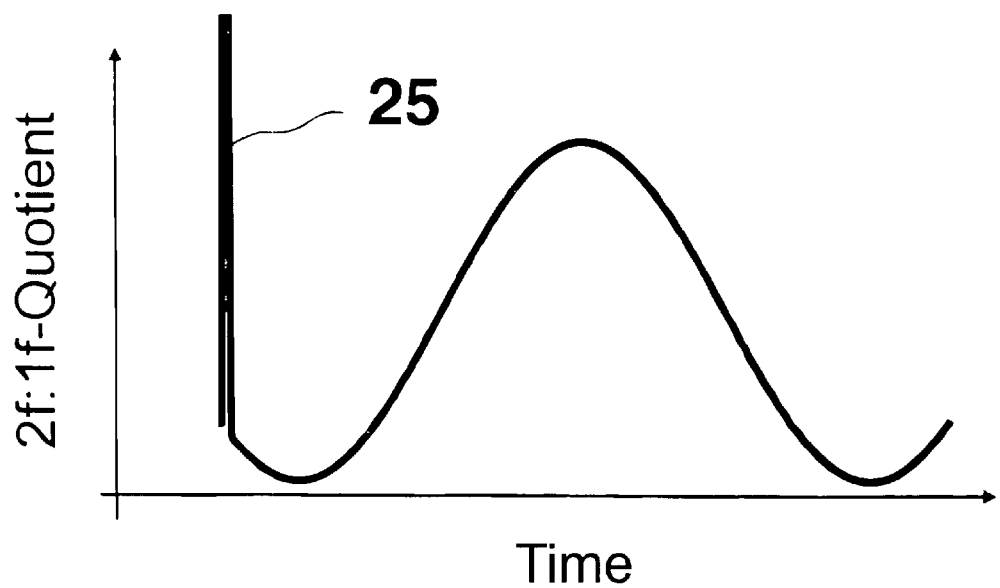

The capability of transmitting additional data from the light source unit 1 to the detector unit 2 with the measuring light can be utilized to realize the above-described starting pulse for synchronization by means of a suitable modulation of the measuring light, as schematically shown in FIGS. 4($a$) and ($b$). At the beginning of a scan, the light source 3 is triggered by the control and evaluation device 6 in such a way that a briefly very high value of the $2f{:}1f$ quotient with a characteristic pulse shape 25 is generated, which can be identified in the detector signal by the control and evaluation device 11 in the detector unit 2 and can be used in the evaluation of the measuring signals for synchronization.

What is claimed is:

1. A gas sensor with an open optical measurement path for optical measurement of at least one gas component, the sensor comprising:

a light source unit, a detector unit, the optical measurement path extending between the light source unit and the detector unit, and first and second control and evaluation devices arranged in the light source unit and the detector unit, respectively, wherein the light source unit has a light source and optical guide elements for transmitting a measuring light beam to the detector unit, and the detector unit includes a detector, which when oriented in the beam path of the measuring light beam detects the intensity of light from the measuring light beam, and the first and second control and evaluation devices determine, on the basis of a detection of the measuring light beam by the detector, a measure for a concentration of a gas component to be investigated, wherein the detector unit is provided with a transmitter device, which communicates with the second control and evaluation device in the detector unit, and the light source unit is provided with a receiver device, which communicates with the first control and evaluation device in the light source unit, so that a direct data exchange between the detector unit and the light source unit is made possible, wherein the light source unit is provided with a transmitter device which communicates with the first control and evaluation device in the light source unit, and the detector unit is provided with a receiver device, which communicates with the second control and evaluation device in the detector unit, so that the direct data exchange between the detector unit and the light source unit is bidirectional, and wherein the optical guide elements in the light source unit are adjustable in their orientation via electrical triggering, and that further optical guide elements in the detector unit are present, which are adjustable in their orientation via electrical triggering, and that the first control and evaluation device in the light source unit and the second control and evaluation device in the detector unit cooperate so that by utilizing the data exchange between the light source unit and the detector unit, they automatically perform an optimal optical calibration by controlling the orientation of the optical guide elements.

2. The gas sensor of claim 1, wherein a pair of cooperating transmitter and receiver devices for wireless data transmission has a light source and a sensor that responds to the light of the light source.

3. The gas sensor of claim 1, wherein a pair of cooperating transmitter and receiver devices has a cable connection.

4. The gas sensor of claim 3, wherein the cable connection includes an electrically conductive cable or a fiber optic cable, and the transmitter device transmits electrical signals or light signals and the receiver device responds to electrical or light signals.

5. The gas sensor of claim 1, wherein the transmitter device in the light source unit and the receiver device in the detector unit are realized in that the first control and evaluation device in the light source unit is designed such that, via a light source controller, it modulates the frequency and/or amplitude of the light emitted by the light source, in order to transmit data from the light source unit to the detector unit, and the second control and evaluation device in the detector unit is correspondingly designed to demodulate the modulation of the measuring light beam and thereby to decode the transmitted data.

6. A gas sensor of claim 1, wherein the transmitter and receiver devices in the light source unit and the transmitter and receiver devices in the detector units are arranged for wireless transmission of data.

7. A gas sensor with an open optical measuring path for the optical measurement of at least one gas component, the gas sensor comprising:

a light-source unit; and a detector unit, the optical measuring path extending between the light source unit and the detector unit;

wherein the light source unit comprises a light source and optical guide elements for sending out a beam of measuring light to the detector unit, the detector unit comprises a detector which, when aligned in the beam path of the beam of measuring light, registers the intensity of light from the beam of measuring light, first and second controlling and evaluating devices are respectively provided in the light source unit and the detector unit for determining, on the basis of the registered signal of the detector, a measure of the concentration of the gas component to be investigated, and controlling the light source unit and the detector unit, the light source unit includes a transmitter device which is linked to the first controlling and evaluating device in the light-source unit, the detector unit includes a receiver device which is linked to the second controlling and evaluating device in the detector unit, the detector unit additionally includes a transmitter device which is linked to the second controlling and evaluating device in the detector unit, the light-source unit additionally includes a receiver device which is linked to the first controlling and evaluating device in the light-source unit, so that a direct bidirectional exchange of data between detector unit and light-source unit is made possible, the optical guide elements in the light-source unit are capable of being adjusted in their alignment, further optical guide elements are provided in the detector unit which are capable of being adjusted in their alignment, and the controlling and evaluating devices are arranged to interact in such a way as to perform an optimal optical adjustment automatically by controlling the alignment of the optical guide elements through the exchange of data between the light-source unit and the detector unit.

8. A gas sensor according to claim 7, wherein at least one pair of transmitter and receiver devices in the light-source unit and in the detector unit is arranged for wireless transmission of data.

9. A gas sensor according to claim 8, wherein the pair of interacting transmitter and receiver devices comprises a light source and a sensor responding to the light of the light source.

10. A gas sensor according to claim 7, wherein a pair of interacting transmitter and receiver devices are connected by a cable.

11. A gas sensor according to claim 10, wherein the cable connection comprises an electrically conductive cable or an optical-fiber cable and the transmitter device transmits electrical signals or light signals and the receiver device responds to the electrical signals or light signals.

12. A gas sensor according to claim 7, wherein the transmitter device in the light-source unit and the receiver device in the detector unit are realized by the first controlling and evaluating device in the light-source unit being arranged in such a way that via a light-source control the first controlling and evaluating device modulates the frequency and/or amplitude of the light emitted from the light source in order to transmit data from the light-source unit to the detector unit, and by the second controlling and evaluating device in the detector unit being arranged to demodulate the modulation of the beam and measuring light and thereby to decode the transmitted data.

* * * * *